United States Patent
Müller

[11] Patent Number: 5,927,978
[45] Date of Patent: Jul. 27, 1999

[54] SYSTEM FOR PLACING A TOOTH REPLACEMENT PART INTO A PATIENT'S MOUTH AND PACKAGING SYSTEM THEREFORE

[75] Inventor: Frank Müller, Klaus, Austria

[73] Assignee: Ivoclar AG, Schaan, Liechtenstein

[21] Appl. No.: 08/920,940

[22] Filed: Aug. 29, 1997

Related U.S. Application Data

[60] Provisional application No. 60/038,912, Feb. 26, 1997.

[30] Foreign Application Priority Data

Sep. 6, 1996 [DE] Germany ............. 196 36 281

[51] Int. Cl.⁶ .................................................. A61C 3/00
[52] U.S. Cl. ............................................ 433/141; 433/147
[58] Field of Search ........................ 433/141 OR, 146, 433/147, 172, 173; 206/63.5, 83, 368, 369

[56] References Cited

U.S. PATENT DOCUMENTS

| | | | |
|---|---|---|---|
| 3,368,553 | 2/1968 | Kirby | 433/146 |
| 3,468,031 | 9/1969 | Mumaw | 433/146 |
| 4,043,042 | 8/1977 | Perfect | 433/90 |
| 5,040,981 | 8/1991 | Oliva | 433/141 |
| 5,062,800 | 11/1991 | Niznick | 433/173 |
| 5,221,202 | 6/1993 | James | 433/9 |
| 5,256,064 | 10/1993 | Riihimaki et al. | 433/141 |
| 5,290,171 | 3/1994 | Daftary et al. | 433/141 |
| 5,320,533 | 6/1994 | Lee | 433/215 |
| 5,569,037 | 10/1996 | Moy et al. | 433/172 |
| 5,636,736 | 6/1997 | Jacobs et al. | 206/369 |

FOREIGN PATENT DOCUMENTS

| | | |
|---|---|---|
| 44 39 410 A1 | 5/1996 | Germany . |
| 196 02 500 A1 | 7/1997 | Germany . |

*Primary Examiner*—John J. Wilson
*Attorney, Agent, or Firm*—John C. Thompson; Alan S. Korman

[57] ABSTRACT

A system for receiving a tooth replacement part and placing the tooth replacement part into a patient's mouth, with the tooth replacement part having a securing projection, includes a holder having at least one recess and an adapter having a connecting portion detachably connected to the at least one recess of the holder. The adapter has a cutout for positive-lockingly receiving the securing projection of the tooth replacement part. A packaging system for the tooth replacement parts includes a container. An adapter is provided for each tooth replacement part. The adapter has a cutout for receiving the securing projection of the tooth replacement part and has a connecting portion opposite the cutout. The container has a removal opening for selectively allowing access to the connecting portion of the adapter placed into the container. The connecting portion is detachably connectable to the holder insertable through the removal opening.

26 Claims, 4 Drawing Sheets

SYSTEM FOR PLACING A TOOTH REPLACEMENT PART INTO A PATIENT'S MOUTH AND PACKAGING SYSTEM THEREFORE

This application claims the benefit of U.S. Provisional Application No. 60/038,912, filed Feb. 26, 1997.

BACKGROUND OF THE INVENTION

The present invention relates to a system for receiving a tooth replacement part and placing (transferring) the tooth replacement part into a patient's mouth. The tooth replacement part has a securing projection. The system includes a holder for transferring and placing the tooth replacement part into the patient's mouth. The correlated packaging system is designed to receive a plurality of tooth replacement parts of the aforementioned kind.

A system for receiving and transferring tooth replacement parts is known from German Patent Application 196 02 500.1. An insert or inlay is provided with a securing projection for handling it which is designed to ensure safe attachment of a holder so that the small, and thus difficult to manipulate, inlay or insert can be removed from its packaging and can be introduced into the prepared cavity of a tooth to be restored. For example, the insert or inlay may be 1 mm thick and may have a length and width of 3 mm. Due to its small size and the resulting difficulty in handling it with tweezers, which must engage the insert at its wide sides, it is known to provide the insert or inlay with a securing projection in the form of a peg or pin which after completed insertion and cementing of the insert or inlay within the tooth is removed.

Such a rounded securing projection is, however, difficult to engage by tweezers especially in view of the fact that an exact positioning of the insert within the tooth cavity is required. It is thus known, for example, from German Offenlegungsschrift 44 39 410, to provide a holder which is to be attached with a clamping element made of an elastic material onto the securing projection to thereby securely hold the tooth replacement part. The clamping element provides a certain press-fit on the securing projection which improves the holding action, but, on the other hand, makes it more difficult to introduce the securing projection with the insert or inlay.

Furthermore, there is the risk that, despite the clamping action of the clamping element, the insert or inlay can be lost and swallowed by the patient if accidentally hitting an obstacle within the mouth of the patient. In the worst case the inlay or insert could even be inhaled by the patient. Thus, in this suggested technical solution, the clamping action must be very strong which, however, makes it more difficult to remove the holder after completed insertion of the inlay or insert especially in view of the fact that, after positioning within the tooth cavity, not even the slightest displacement of the tooth replacement part should occur.

A further problem of this known tooth replacement part is that the insertion of the securing projection into the clamping element, because of its smaller size, is not very easily performed. In this context, there is also the problem that the tooth replacement part must remain sterile. In some cases, the tooth replacement parts are coated with a silane coating so that they cannot be handled by hand in order not to endanger the bonding to the composite material. Such a tooth replacement part has been suggested already with the aforementioned German Patent Application P 196 02 500.1.

It is therefore an object of the present invention to provide a system of the aforementioned kind as well as a packaging system of the aforementioned kind which allows for a risk-free but comfortable and inexpensive as well as hygienic handling of the tooth replacement part and which also meets the day-to-day requirements of a dental practice.

SUMMARY OF THE INVENTION

A system for receiving a tooth replacement part and placing the tooth replacement part into a patient's mouth, wherein the tooth replacement part has a securing projection, according to the present invention is primarily characterized by:

A holder having at least one recess;

An adapter having a connector portion detachably connected to the at least one recess of the holder;

The adapter having a cutout for positive-lockingly receiving the securing projection of the tooth replacement part.

Advantageously, the tooth replacement part is an insert or an inlay.

The securing projection of the tooth replacement part is detachably received in the cutout, wherein the adapter is a coupling between the holder and the securing projection.

Preferably, the cutout of the adapter has an undercut for engaging a matching undercut of the securing projection.

Preferably, the cutout is positioned at a first end of the adapter remote from the connecting portion and the adapter, at least in the area of the cutout consists of an elastic material.

Advantageously, the securing projection is positive-lockingly secured in the cutout. Alternatively, the securing portion is frictionally secured in the cutout.

The securing projection may be positive-lockingly and frictionally secured in the cutout.

Expediently, the securing projection and the cutout have a matching mushroom shape.

Advantageously, the securing projection has a head portion and a neck portion received in matching portions of the cutout. The head portion is held in the cutout with play and the neck portion is held in the cutout by press-fit.

The tooth replacement part is securely held in the adapter and is removable from the adapter, after being placed into a cavity of a patient's tooth, by pivoting the adapter relative to the tooth replacement part by pressing against the cavity.

The connecting portion is a snap-on connector providing a frictional connection between the adapter and the holder.

The holder has two of the recesses for receiving the snap-on connector such that the adapter is connectable to the holder in two connecting positions that are 180° displaced relative to one another.

The holder consists preferably of a dimensionally stable material and the adaptor consists of a material that is less stiff than the dimensionally stable material. The holder comprises a handle and the handle is preferably positioned angularly to the main body of the holder.

The handle is preferably positioned at an angle of 70° relative to the main body.

The present invention also relates to a packaging system for tooth replacement parts characterized according to the present invention by:

A container for receiving tooth replacement parts, wherein the tooth replacement parts have a securing projection;

An adapter for each tooth replacement part;

The adapter having a cutout for receiving the securing projection of a tooth replacement part;

The adapter having a connecting portion opposite the cutout;

The container having a removal opening for selectively allowing access to the connecting portion of the adapter placed in the container, wherein the connecting portion is detachably connectable to a holder insertable through the removal opening.

Advantageously, the container comprises an annular case having individual, circumferentially distributed compartments in the form of depressions, wherein each one of the compartments receives a unit comprised of one of the adapters having a tooth replacement part attached thereto.

Preferably, the container comprises a lid and the removal opening is provided in the lid. The lid is designed such that the removal opening allows access to only one of the compartments while the other compartments are covered.

The annular case comprises a portion free of one of the compartments and the lid has a closing position in which the removal opening is located at the portion free of the compartments.

Expediently, the adapter is supported at the annular case and the tooth replacement part attached to the adapter is positioned in the compartment without contacting the sidewalls of the compartment.

The annular case has abutment surfaces for the adapter and the adapter has matching contact surfaces.

The abutment surfaces are conical.

The abutment surfaces may be upwardly slanted.

The connecting portion and the cutout are designed such that a securing force of the connecting portion is greater than a securing force of the cutout.

The connecting portion is a shaft for insertion into a recess of the holder and comprises a slanted insertion portion.

Each one of the units is preferably coded for identifying characteristics of the tooth replacement part such as color and shape.

The units are preferably color-coded for identifying purposes.

The inventive system for receiving and transferring a tooth replacement part is primarily characterized in that a manipulation of the tooth replacement part without contact and thus in a sterile fashion is possible. Accordingly, the holder is snapped onto the inventor adapter, respectively, to its shaft. The shaft of the adapter securely snaps into a corresponding opening of the holder whereby the snap-on connection in a preferred embodiment of the invention preferably allows for two positions which are usable as a distal and as a mesial position depending on whether the insert is to be used on the distal or mesial side of the tooth.

The inventive system suggests that the securing portion of the tooth replacement part is secured in the cutout of the adapter. Preferably, the tooth replacement parts are inlays or inserts. The securing projection is preferably positive-lockingly secured within the cutout of the adapter. By doing so, it is possible to reduce the clamping action to such an extent that the clamping force relative to a purely frictional connection can be reduced to the required minimum. The insertion of the insert or inlay is carried out preferably with a slight rotational movement which widens, the elastic walls of the cutout of the adapter and which thus releases the securing projection readily. It is understood that the lateral pressure acts in the direction of the tooth to be restored and a release of the insert from the tooth cavities is thus prevented. This movement corresponds substantially to the movement required for properly operating a spatula and thus is well known to a dentist and does not require any training.

According to an alternative embodiment, the insert or inlay is gripped with tweezers and is slightly pressed against the adapter. The release from the adapter cutout is then easily achieved with a simple pivoting or tilting movement of the holder. The adapter thus serves as a coupling between the securing projection of the tooth replacement part and the holder. In principle, any connection between the adapter and the two other parts is possible that allows for a detachable connection.

In an especially preferred embodiment it is suggested that the securing projection is substantially mushroom-shaped. Due to the circular design, a tilting movement in any suitable direction is possible and the press-fit between the neck portion of the securing projection and the corresponding area of the cutout thus only requires a rather minimal pressing force which is only slightly greater than a contacting force and which serves to secure the securing projection in a play-free manner.

It is understood that the securing force of the shaft within the holder is selected such that the required maneuvering of the adapter with inserted tooth replacement part is possible without the risk of detachment so that the securing force of the adapter within the holder is always greater than the securing force of the adapter at the tooth replacement part. In this context, it is especially advantageous that according to the inventive packaging system individual compartments are provided which provide a secure support for the adapter so that without problems a great pressure can be exerted onto the packaging system when snapping on the holder onto the adapter without affecting the sterile tooth replacement part. Preferably, the adapter is placed onto the securing projection of the tooth replacement part and subsequently the tooth replacement part is introduced into a bath in order to apply a silane coating thereon. Subsequently, the tooth replacement part is introduced into the packaging container.

In this context, it is especially advantageous when the tooth replacement part is held in the individual compartment without contacting the sidewalls. The adapter is preferably secured on a conical support surface.

According to a further especially advantageous embodiment the packaging system comprises a container having individual compartments that can be selectively accessed. A lid can be arranged such that it can be displaced to one side when a rectangular packaging container (case) is provided or rotated when a round or annular packaging container (case) is used. The lid is provided with a removal opening that allows access to exactly one individual compartment in order to allow removal of the unit of adapter and tooth replacement part.

Preferably, it is suggested that the packaging system when delivered comprises in each one of the individual compartments a combination (unit) of an adapter with tooth replacement part suspended therefrom. According to a further especially advantageous embodiment, the adapter is comprised of a transparent or at least translucent plastic material. It can be reintroduced, after placing the tooth replacement part into the tooth cavity, into the empty individual compartment. It is then visible whether the tooth replacement part has already been removed or not.

According to another embodiment, the packaging container is translucent or transparent in areas that are positioned lateral to the tooth replacement part so that it can be checked from the exterior whether the tooth replacement part is still contained in the container or whether there is only an empty adapter present. The thus embodied packaging system also allows to reuse the packaging container together with the adapters after subjecting them to a sterilization process. The adapters can be premounted together with the insert or inlay. They can be color-coded in order to provide identification in regard to shape or color of the insert or inlay.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1 through 4.

Figure 1:
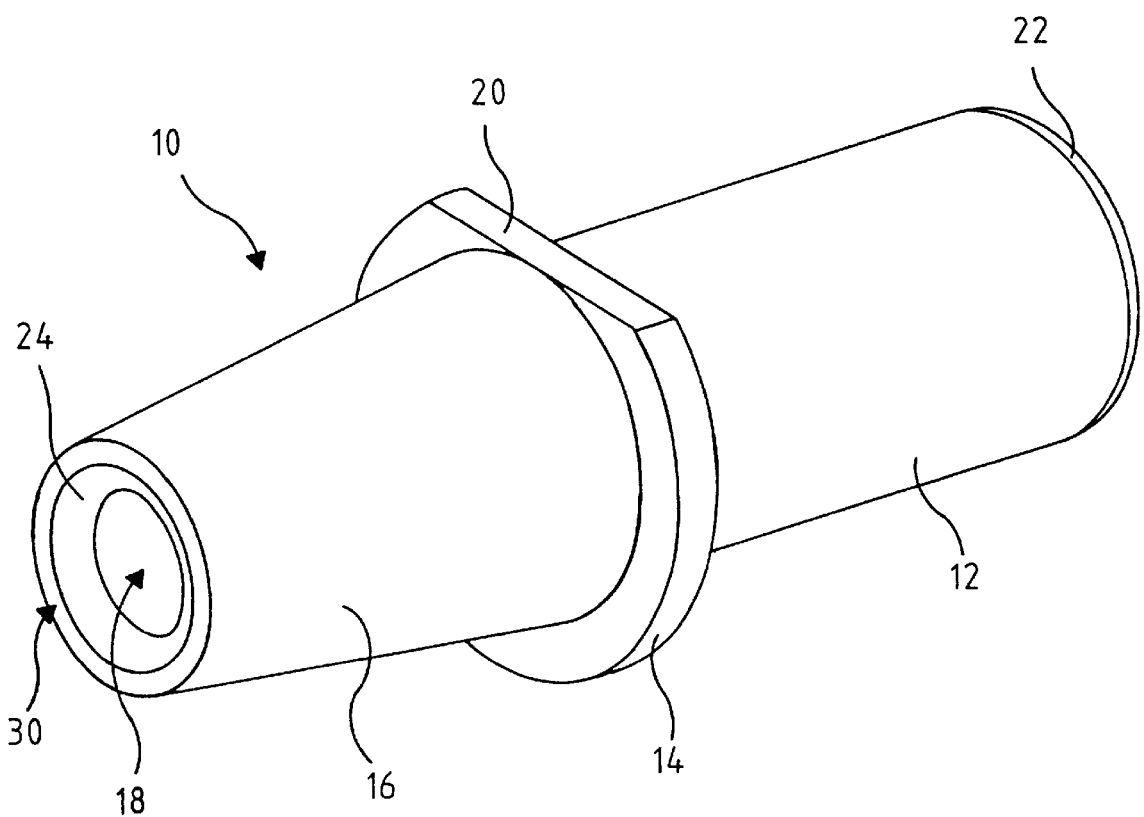
FIG. 1 shows a perspective view of an embodiment of the inventive adapter.
Figure 4:
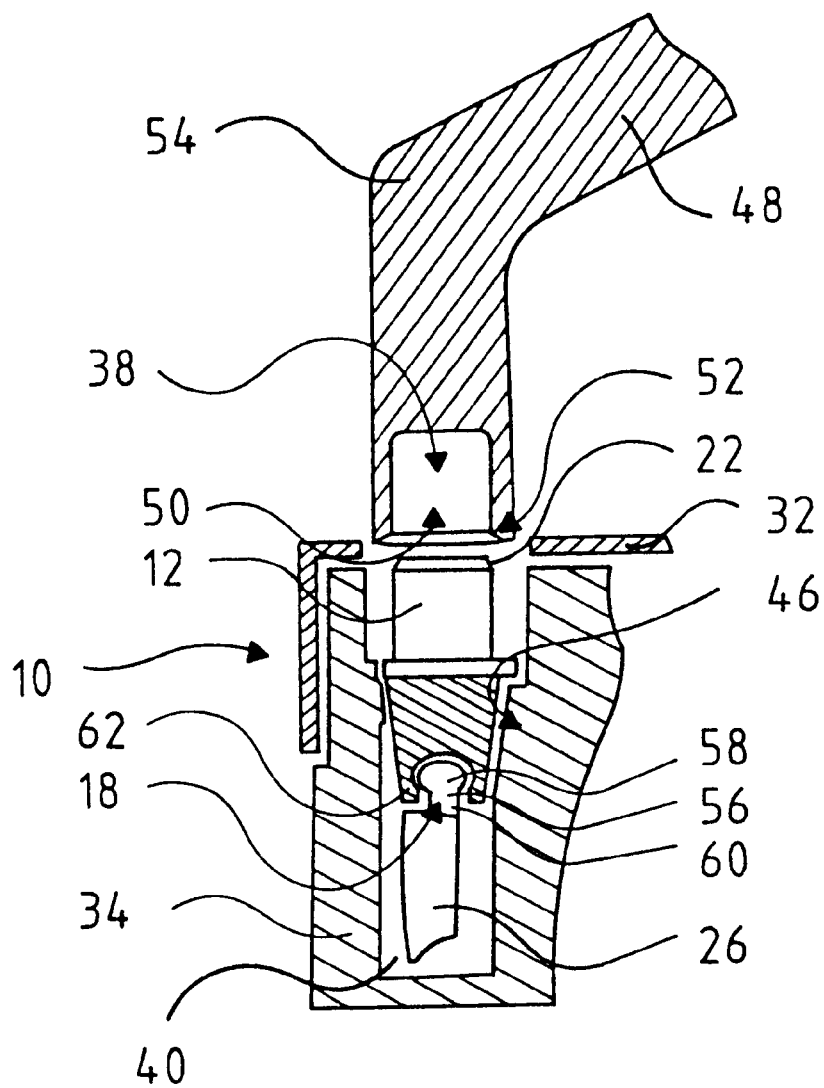
FIG. 4 shows a cross-sectional view of the inventive receiving and transferring system, before introduction of the holder, still within the individual compartment of the inventive packaging system.

The embodiment of an adapter 10 represented in FIG. 1 comprises a connecting portion or shaft 12 for the holder shown in FIG. 4. It has a flange 14, an outer cone 16 as well as a cutout 18 for receiving the tooth replacement part shown in FIG. 2. The connecting portion 12 is elliptically shaped and fits a corresponding recess in the holder whereby it is understood that two snap-on positions are possible which are displaced relative to one another by 180°. The snap-on positions are specified as mesial and distal and serve for improved manipulation, depending on whether an insert is to be introduced into the mesial or distal area of a molar or premolar. The flange 14 serves as an abutment for the snap-on position of the holder and comprises a flat portion 20 with which the snap-on position can be detected from the exterior. The connecting portion 12 furthermore comprises a slanted insertion portion 22 which facilitates its introduction into the holder.

The area of the outer cone 16 is relatively slim whereby the holder has a diameter that does not surpass the diameter of the flange 14 or surpasses it only slightly. The flat portion 20 serves at the same time as a rotational securing means for the tooth replacement part in the individual compartments of the packaging container, as is shown in FIG. 4. Thus, a slim design of the inventive receiving and transferring system is achieved that improves manipulation.

The cutout 18 also comprises a slanted insertion portion in the form of an inner cone 24 which facilitates the preparation in regard to manufacture of the inventive system and the introduction of the tooth replacement part.

Figure 2:
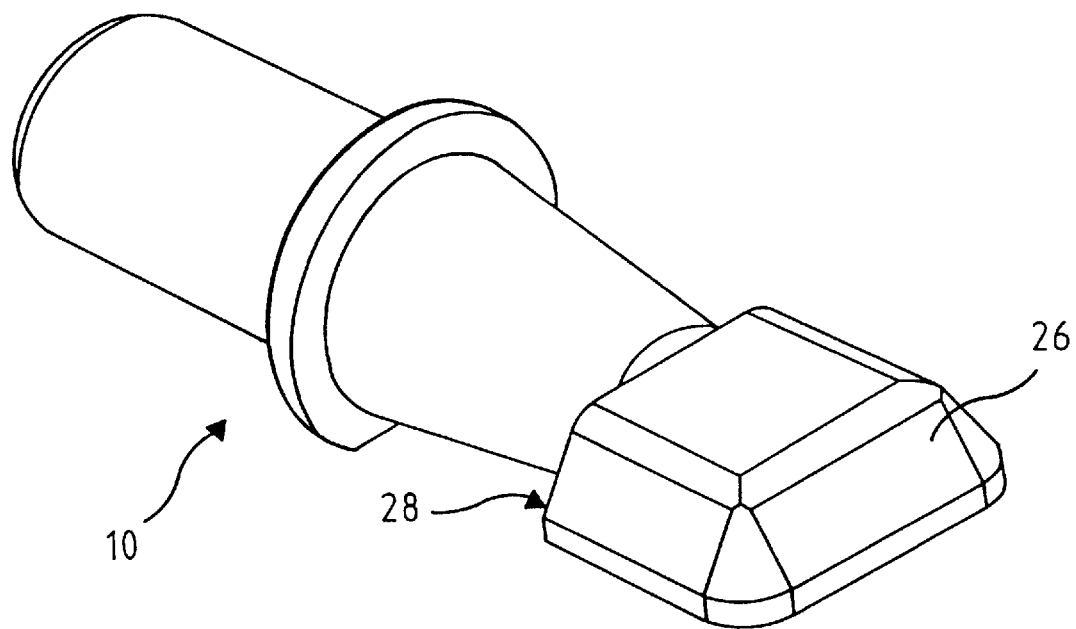
FIG. 2 shows a perspective view of the inventive adapter with inserted tooth replacement part as part of the receiving and transferring system.

FIG. 2 illustrates how a tooth replacement part, in the form of an insert 26, is secured at the adapter 10. A securing projection of the insert 26, not represented in FIG. 29 is introduced into the cutout 18 so that the insert 26 with its upper side is flush with an end face 30 (FIG. 1) of the adapter 10. In this position the insert 26 is securely held at the adapter 10. The adapter is preferably made of a plastic material which has soft elastic properties, for example, it consists of a correspondingly adjusted polypropylene or polyethylene material.

According to another embodiment, the adapter is color coded in order to be able to identify insert/inlay shapes, respectively, insert/inlay sizes. According to a third embodiment, the different color codings of the adapter can also be used for differentiating the tooth color of the insert, respectively, inlay.

The insert 26 is preferably packaged within the packaging system of FIG. 4 in a sterile manner and optionally is coated with a silane coating in order to ensure improved bonding to the composite material. The slim shape of the combination comprised of holder, adapter 10, and insert 26 allows the dentist also to monitor manipulations since all parts are easily visible.

Figure 3:
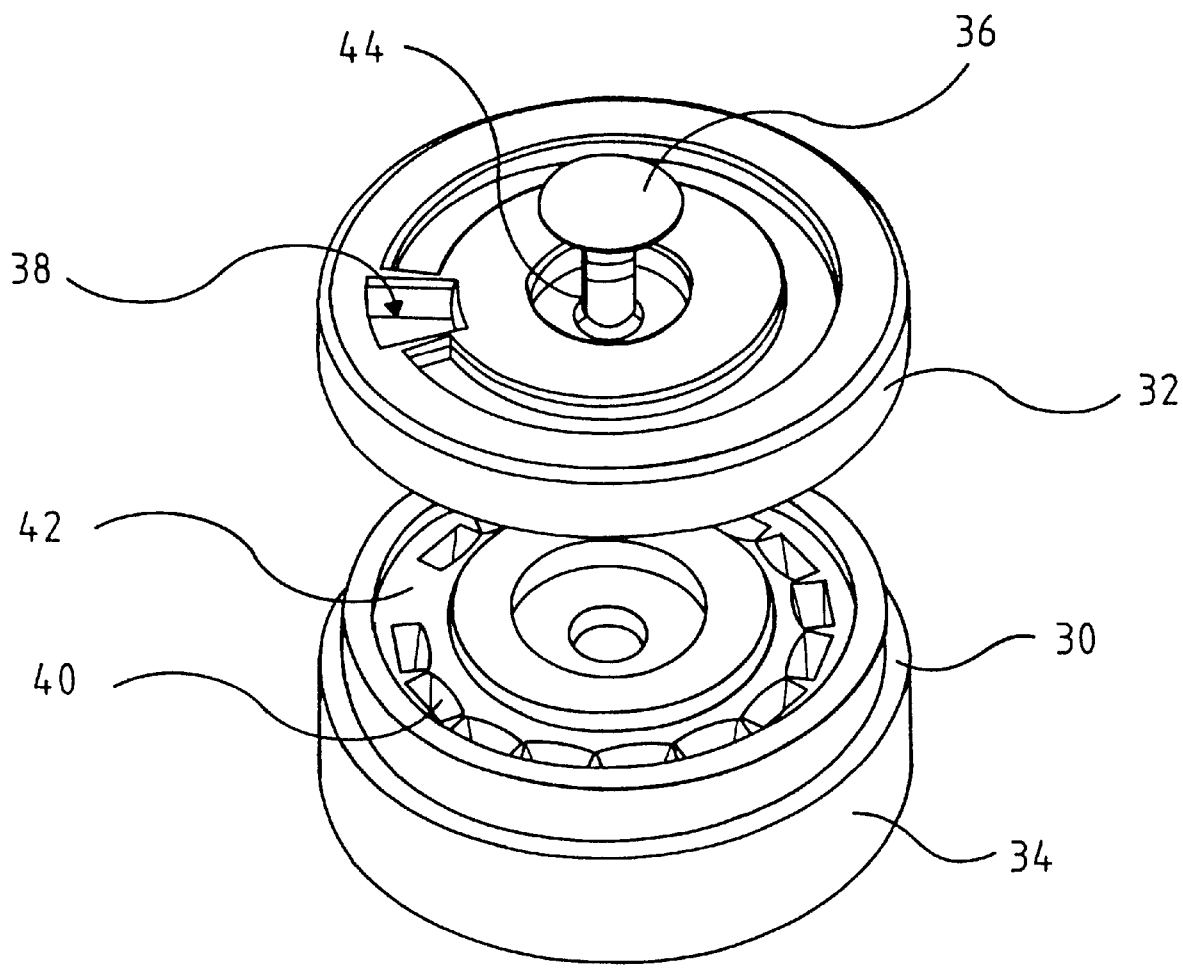
FIG. 3 shows a perspective view of an inventive packaging system before assembly.

In principle, the manipulation of the inventive receiving and transferring system can be used in connection with any suitable packaging unit, for example, a peel bag etc. Inventively, it is preferred to provide a packaging system as shown in FIG. 3 which comprises a packaging container 30 which in the shown embodiment is round but can also be in the form of a rectangular packaging container with a slidable lid. The packaging container 30 comprises a rotating lid 32 and an annular case 34 to which the lid is rotatably connected with a connecting clip 36. The rotatable lid 32 comprises a removal opening 38 which upon rotation of the lid can be positioned such that it allows access to exactly one individual compartment while all the other individual compartments, which are in the form of depressions within the case 34, are covered. Each individual compartment 40 is designed for receiving a combination (unit) composed of an adaptor 10 and a tooth replacement part 26, as can be seen especially in FIG. 4. In addition, a portion 42 is provided that is without compartment so that in a closing position of the lid 32 none of the individual compartments can be accessed. The connecting clip 36 is snapped onto the case 34 of the container 30 and penetrates a central opening 44 of the lid 32 so that the lid 32 is secured at the container 30 but can be easily rotated when needed.

The rotating lid 32 can also be provided with a catch which is not shown in FIG. 3 and which has a width corresponding to the width of an individual compartment so that the removal opening 38 is always caught in a respective aligned position in order to allow access to an individual compartment 40. It is understood that preferably at the portion 42 a depression is provided in order to allow a corresponding catch position for all individual compartments 40.

Even though in FIG. 3 the individual compartments 40 are shown as angular compartments that taper conically, it is preferred to provide the individual compartments 40, as shown in FIG. 4, in the form of substantially round compartments with a slightly flattened portion at one side whereby preferably the upper area of each individual compartment has a support surface 46 for the outer cone 16. The outer cone 16 is then suspended at such a level that the tooth replacement part 26 is freely suspended within the compartment 40 and can be removed without coming into contact with the sidewalls.

As can be seen in FIG. 4, a separate holder 48 is provided which has a recess 50 into which the shaft 12 of the adapter 10 can be introduced. The recess 50 as well as the shaft 12 are of elliptical shape and have corresponding slanted insertion portions 22 and 52. The holder 48 in FIG. 4 is only partly represented and for simplying the manipulation of the system is angled at its angular portion 54, preferably at an angle of 70°.

As can be seen in FIG. 4, the tooth replacement part 26 comprises a securing projection 56 which extends into the cutout 18 of the adapter 10. The securing projection is positive-lockingly secured in the cutout 18 and comprises a mushroom-shaped head portion 58 as well as a neck portion 60 that is secured in matching areas of the cutout. The securing projection 56 can be secured preferably so as to be rotationally fixed within the cutout 18 which is possible by providing a shape that deviates slightly from a circular shape. The adapter 10, due to the tapered design, i.e., its outer cone 16, is comparatively yielding at its forward area so that the inventive actuation for releasing the tooth replacement part 26, after introduction into the tooth cavity, is simply achieved by widening the grip pawls 62 of the adapter. The grip pawls 62 provide an undercut within the cutout 18 of the adapter 10. With some training it is possible with a slight tilting movement to release the tooth replacement part 26 safely and the adapter can then be returned into the individual compartment 40 through the removal opening 38. It is understood that instead of a two-part container it is also possible to use a one-part container whereby the container 30 or the lid 32 can be differently colored or can be marked with a particular color.

The present invention is, of course, in no way restricted to the specific disclosure of the specification and drawings, but also encompasses any modifications within the scope of the appended claims.

What is clamed is:

1. A kit for use in transferring a tooth replacement part from a container into a patient's mouth; the kit comprising:
   a tooth replacement part having a securing projection, the tooth replacement part being selected from a group consisting of inlays and inserts;
   an adapter having a cutout which initially releasably engages the securing projection of the tooth replacement part but which is adapted to be detached from the securing projection after the tooth replacement part has been placed in a patient's mouth, the adapter further being provided with a connecting portion; and
   a holder having a handle and a connecting portion adapted to readily releasably engage the connecting portion of the adapter, the holder being capable of transferring the adapter and the tooth replacement part from a container into a patient's mouth after the connecting portion of the holder has releasably engaged the connecting portion of the adapter.

2. A kit according to claim 1, wherein the securing projection of the tooth replacement part is detachably received in said cutout, wherein said adapter is a coupling between said holder and the securing projection.

3. A kit according to claim 1, wherein said cutout of said adapter has an undercut for engaging a matching undercut of the securing projection.

4. A kit according to claim 1, wherein said cutout is positioned at a first end of said adapter remote from said connecting portion and wherein said adapter, at least in the area of said cutout, consists of an elastic material.

5. A kit according to claim 1, wherein the securing projection is positive-lockingly secured in said cutout.

6. A kit according to claim 1, wherein the securing projection is frictionally secured in said cutout.

7. A kit according to claim 1, wherein the securing projection is positive-lockingly and frictionally secured in said cutout.

8. A kit according to claim 1, wherein the securing projection and said cutout have a matching mushroom shape.

9. A kit according to claim 8, wherein the securing projection has a head portion and a neck portion received in matching portions of said cutout, wherein the head portion is held in said cutout with play and wherein the neck portion is held in said cutout by press-fit.

10. A kit according to claim 1, wherein the tooth replacement part is securely held in said adapter and is removable from said adapter, after being placed into a cavity of a patient's tooth, by pivoting said adapter relative to the tooth replacement part by pressing against the cavity.

11. A kit according to claim 1, wherein said connecting portion of the adapter is a snap-on connector providing a frictional connection between said adapter and said holder.

12. A kit according to claim 11, wherein the connecting portion of said holder has a recess for receiving said snap-on connector such that said adapter is connectable to said holder in one of two connecting positions that are 180° displaced relative to one another.

13. A kit according to claim 1, wherein said holder consists of a dimensionally stable material and said adapter consists of a material that is less stiff than said dimensionally stable material, wherein said holder comprises a handle and wherein said handle is positioned angularly to a main body of said holder.

14. A kit according to claim 13, wherein said handle is positioned at an angle of 70° relative to said main body.

15. A kit for use in transferring a tooth replacement part from a container into a patient's mouth; the kit comprising:
   a tooth replacement part having a securing projection, the tooth replacement part being selected from a group consisting of inlays and inserts;
   an adapter having a cutout for releasably engaging the securing projection of the tooth replacement part but which is adapted to be detached from the securing projection after the tooth replacement part has been placed in a patient's mouth, the adapter further being provided with a connecting portion;
   a holder having a handle and a connecting portion; and
   a container initially having a tooth replacement part and an adapter mounted therein, the adapter initially releasably engaging the securing projection of the tooth replacement part, the container having a removal opening for selectively allowing access to the connecting portion of the adapter wherein the holder may readily releasably engage the connecting portion of the adapter, the holder being capable of transferring the adapter and the tooth replacement part from the container into a patient's mouth after the connecting portion of the holder has releasably engaged the connecting portion of the adapter.

16. A kit according to claim 15, wherein said container comprises an annular case having individual, circumferentially distributed compartments in the form of depressions, wherein each one of said compartments receives a unit comprised of one of said adapters having a tooth replacement part attached thereto.

17. A kit according to claim 15, wherein said container comprises a lid and wherein said removal opening is provided in said lid, said lid designed such that said removal opening allows access to only one of said compartments while the other ones of said compartments are covered.

18. A kit according to claim 17, wherein said annular case comprises a portion free of one of said compartments and wherein said lid has a closing position in which said removal opening is located at said portion free of one of said compartments.

19. A kit according to claim 15, wherein said adapter is supported at said annular case and wherein the tooth replacement part attached to said adapter is positioned in said compartment without contacting a wall of said compartment.

20. A kit according to claim 19, wherein said annular case has abutment surfaces for said adapters and wherein said adapters have matching contact surfaces.

21. A kit according to claim 20, wherein said abutment surfaces are conical.

22. A kit according to claim 20, wherein said abutment surfaces are upwardly slanted.

23. A kit according to claim 15, wherein said connecting portion of the adapter and said cutout are designed such that a securing force of said connecting portion is greater than a securing force of said cutout.

24. A kit according to claim 15, wherein said connecting portion of the adapter is a shaft for insertion into a recess of the holder and comprises a slanted insertion portion.

25. A kit according to claim 15, wherein each one of said units is coded for identifying characteristics of the tooth replacement part, including color and shape.

26. A kit according to claim 25, wherein said units are color-coded for identifying the characteristics.

* * * * *

UNITED STATES PATENT AND TRADEMARK OFFICE
CERTIFICATE OF CORRECTION

PATENT NO. : 5,927,978
DATED : July 27, 1999
INVENTOR(S) : Frank Muller

It is certified that error appears in the above-indentified patent and that said Letters Patent is hereby corrected as shown below:

In claims 17, 19, 23, and 24, line 1 of each claim, change "15" to --16--.

Signed and Sealed this

Sixteenth Day of May, 2000

Attest:

Q. TODD DICKINSON

Attesting Officer

Director of Patents and Trademarks